United States Patent [19]

Aid

[11] Patent Number: 4,574,876
[45] Date of Patent: Mar. 11, 1986

[54] CONTAINER WITH TAPERED WALLS FOR HEATING OR COOLING FLUIDS

[75] Inventor: James D. Aid, St. Petersburg, Fla.

[73] Assignee: Extracorporeal Medical Specialties, Inc., King of Prussia, Pa.

[21] Appl. No.: 537,314

[22] Filed: Sep. 29, 1983

Related U.S. Application Data

[60] Continuation-in-part of Ser. No. 394,582, Jul. 2, 1982, which is a division of Ser. No. 262,162, May 11, 1981, abandoned.

[51] Int. Cl.[4] .......................... F28F 21/06; F28B 9/10
[52] U.S. Cl. ...................................... 165/46; 165/170; 165/917
[58] Field of Search ................. 165/46, 146, 147, 170, 165/114, DIG. 24

[56] References Cited

U.S. PATENT DOCUMENTS

| | | | |
|---|---|---|---|
| 1,958,899 | 5/1934 | MacAdams | 165/146 |
| 2,934,322 | 4/1960 | Hazard | 165/147 |
| 3,022,781 | 2/1962 | Andrassy | 126/426 |
| 3,485,295 | 12/1969 | Hrdina | 165/147 |
| 4,059,095 | 11/1977 | Grundmann et al. | 126/426 |
| 4,146,012 | 3/1979 | Elkins et al. | 126/426 |
| 4,153,501 | 5/1979 | Fink et al. | 165/146 X |
| 4,287,876 | 9/1981 | Jacques | 126/426 |

Primary Examiner—Sheldon J. Richter
Attorney, Agent, or Firm—Mark A. Hofer

[57] ABSTRACT

Flexible container means for the warming or cooling of fluids. A preferred embodiment, useful for the warming of plasma following cryogellation techniques prior to its return to the patient, comprises container means formed by the heat sealing of polymeric materials thereby defining a winding passageway of tapered walls whereby the container becomes air self-evacuating.

4 Claims, 12 Drawing Figures

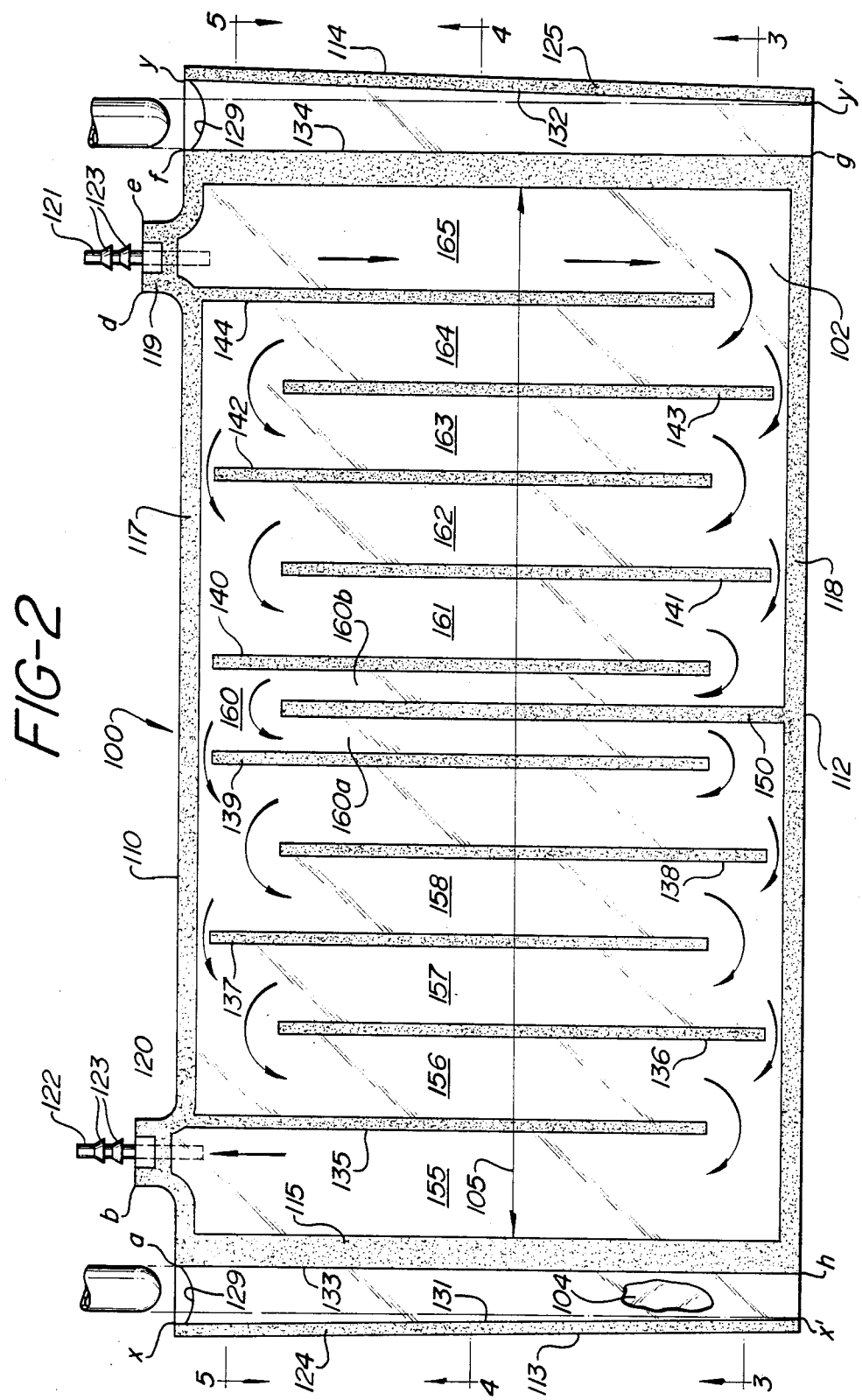

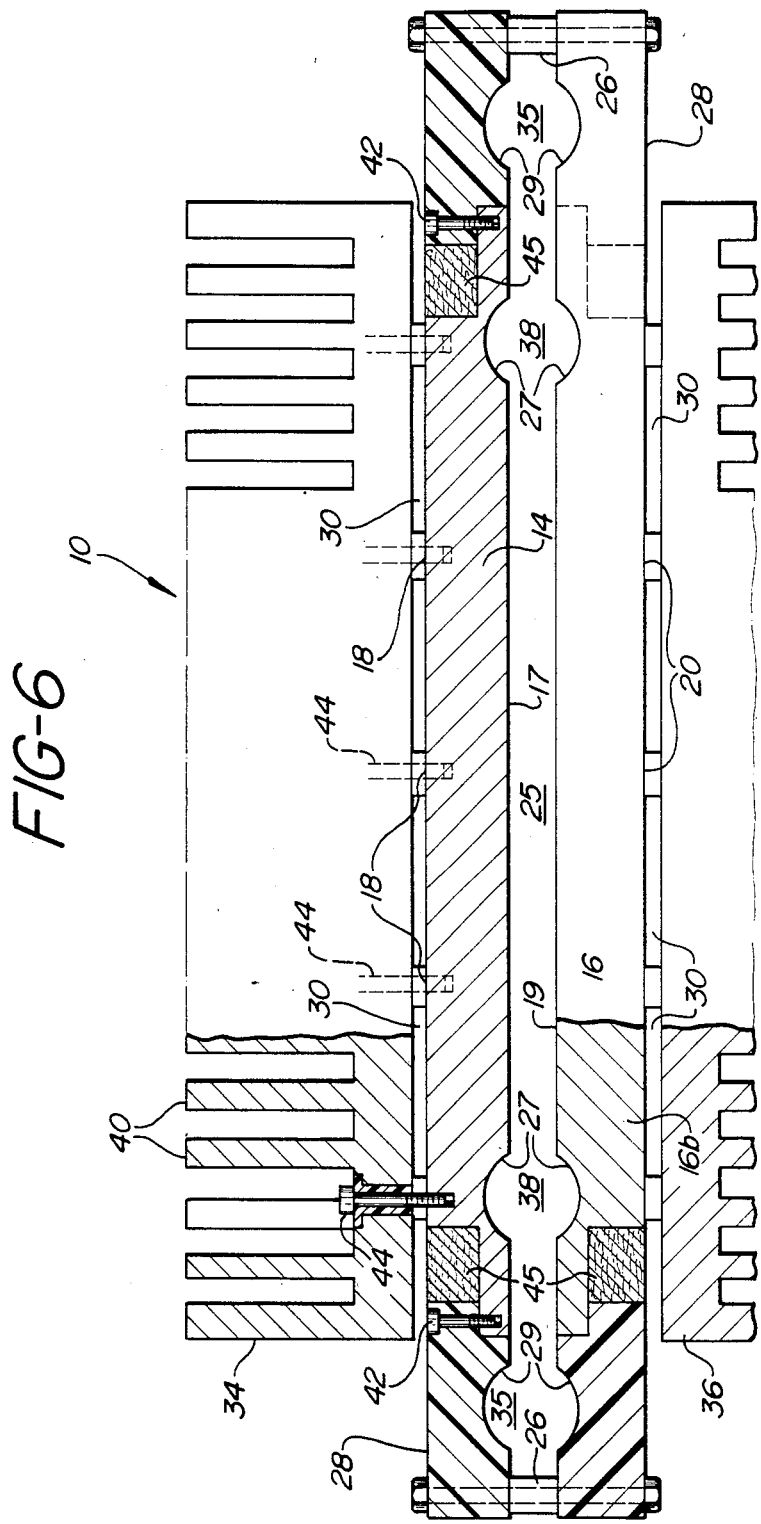

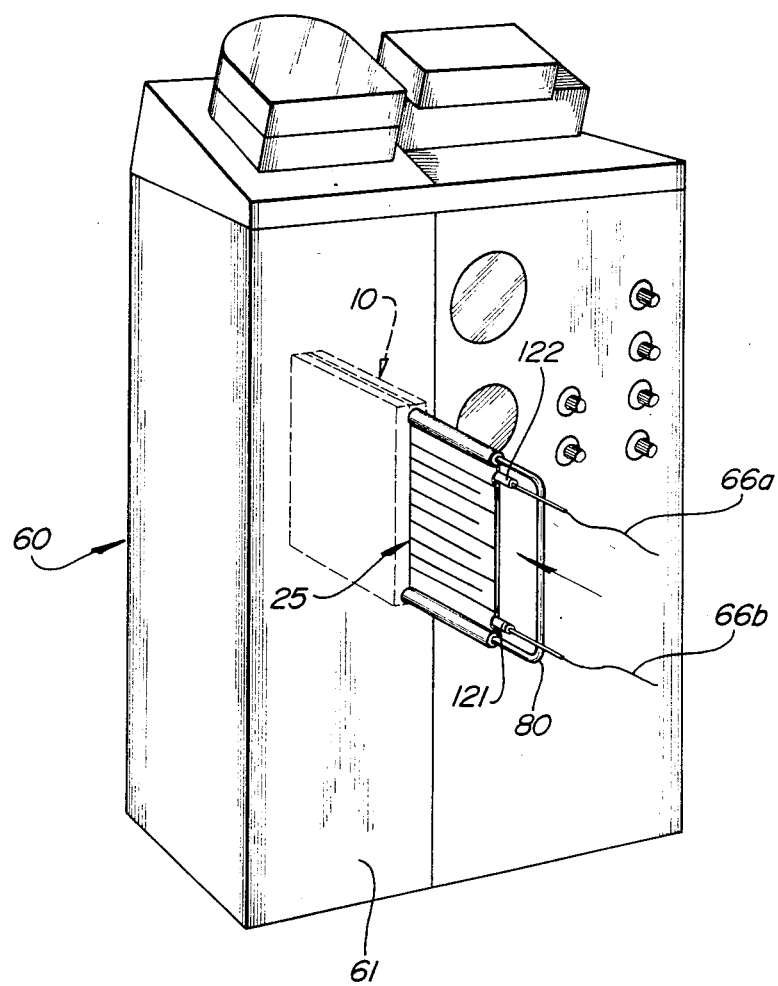

CONTAINER WITH TAPERED WALLS FOR HEATING OR COOLING FLUIDS

BACKGROUND OF THE INVENTION

This application is a continuation-in-part of U.S. Ser. No. 394,582 filed July 2, 1982, still pending which is a divisional application of U.S. Ser. No. 262,162 filed May 11, 1981 and now abandoned.

The present invention relates to apparatus for heating or cooling liquids. More particularly, it relates to apparatus for heating or cooling physiological fluids, such as whole blood and blood plasma, or liquids, such as dialysis fluid, which are used in the treatment of such physiological fluids. It also relates to containers in which or through which such fluids may be contained or circulated in order to effect heating or cooling.

It is frequently necessary or advisable during the course of medical treatment to heat or cool physiological fluids or to heat or cool liquids which are used in the treatment of such physiological fluids. For example, in haemodialysis it is common practice to heat the dialysis fluid before it enters the blood dialyzer. In heart-/lung bypass surgery employing a blood oxygenator, blood which has been oxygenated outside the body is generally rewarmed to about body temperature before being returned to the patient. In the collection of whole blood from donors, it is sometimes desirable to cool the collected blood prior to further processing. Similarly, in plasmapheresis, where blood is taken from a donor and separated by centrifugation or membrane filtration into a fraction comprising cellular components and a fraction comprising plasma, it is desirable to have heating apparatus or cooling apparatus available prior to further handling of the separated fractions. As an example, if the cellular component fraction is to be returned to the patient, either as such or with a specified volume of replacement fluid added thereto, it would be advantageous to warm same to approximately body temperature prior to such return. On the other hand, apparatus for cooling may be needed if the separated plasma fraction is to be subjected to further processing such as filtration or treatment with an absorbent substance. It will also be recognized that in some circumstances heating or cooling may be needed on a batch basis. Batch heating, for example, may be used in connection with the transfusion of blood; in that case, a bag of blood which has been refrigerated is usually warmed before the patient is transfused. In other circumstances, it may be necessary or desirable to effect heating or cooling on a continuous basis. In blood dialysis, for example, it is customary to heat the dialysate prior to passing it through the dialyzer. In plasmapheresis procedures, it may be desirable to cool either the separated cellular fraction or the separated plasma fraction on a continuous basis.

Further, it is often desirable to process blood components by chilling as a method for treatment of certain diseases. For instance, the pain of rheumatoid arthritis can sometimes be alleviated by removing cryoprecipitates of blood plasma in a cryogellation system. Typically in such a system, the plasma is separated from a patient's whole blood by use of a centrifuge or membrane filter. The temperature of the plasma is quickly reduced thereby causing a change in its solubility resulting in the precipitation of Cryoprecipitate particles out of the chilled solution which may then be readily removed by standard filtration techniques. The filtered plasma is then preferably warmed and added back to the blood solution from which it was removed. The reconstituted whole blood may then be additionally warmed to a temperature suitable for return to the patient.

Other immunologically related diseases are sometimes treated by an extracorporeal plasma exchange process. In a plasma exchange process the plasma is separated from the patient's whole blood and discarded. The discarded plasma is replaced with a plasma fluid obtained from an acceptable donor. The replacement fluid is usually retained in the blood bag, and is preferably warmed prior to mixing with the separated blood solution. Mixing may be accomplished by combining properly proportioned amounts of replacement plasma fluid and separated blood either prior to or during the warming process prior to its return to the patient.

SUMMARY OF THE INVENTION

In accordance with the objects of the present invention, there is provided a generally flexible container means which is advantageously adapted to be removably secured to a frame means. The flexible container means and its accompanying frame member are ideally sized for facile insertion into a space defined by heat conducting means for heating or cooling. Such a frame member may be generally U-shaped and comprises a pair of substantially parallel arm members joined by a cross member.

The container means, which is in the form of a flat bag (when empty), possesses two major walls comprising relatively thin, generally flexible sheets of a polymeric material, and further comprises a pair of tapered, laterally extending, pockets or sleeves for receiving the arms of the frame member. The bag and frame member are sized and constructed so that when the arms of the frame member are inserted into the pockets of the bag, the bag is tensioned therebetween. The tensioning serves to straighten out the leading edge of the bag, thus facilitating its insertion into a relatively narrow space defined by thermally conductive elements of the heating or cooling apparatus.

In a preferred embodiment, the container means further includes a plurality of internal channels, having substantially identical widths, which serve to direct the flow of liquid through the bag in alternating directions.

The foregoing and other features of the present invention will be more readily understood with reference to the accompanying drawings and description. While the apparatus of the present invention is described herein with reference to the heating or cooling of physiological fluids, or with reference to the heating or cooling of liquids which are used to treat such physiological fluids, it will be apparent to those skilled in the art that the apparatus may also be used to heat or cool other types of liquids.

BRIEF DESCRIPTION OF THE DRAWINGS

FIG. 2 is a perspective view of one embodiment of a container means of the present invention;

FIG. 6 is a top view, with some parts in cross-section, other parts enlarged, and still other parts cut away, of an apparatus for heating or cooling;

FIG. 7 is a perspective view showing a container means of the present invention being inserted into a cabinet which includes the apparatus of FIG. 6;

DESCRIPTION OF THE PREFERRED EMBODIMENT

Figure 1:
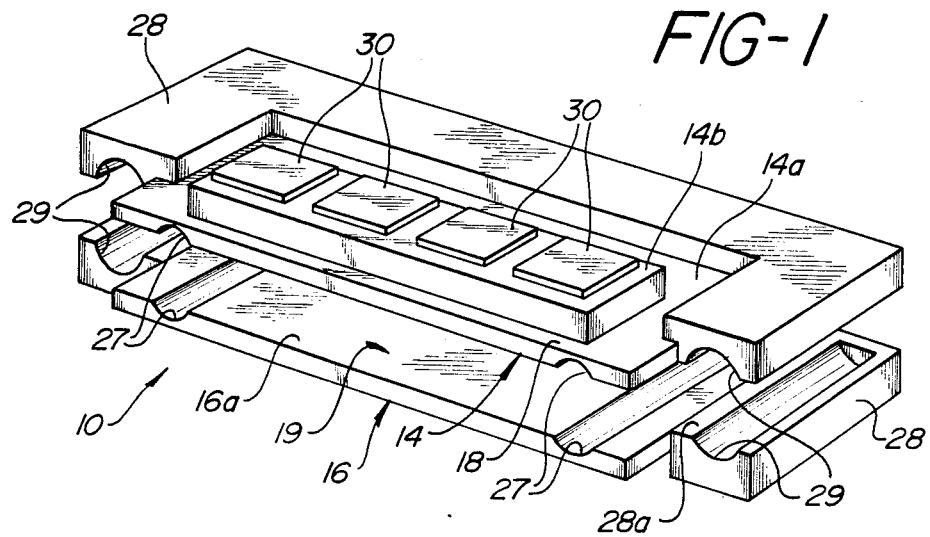
FIG. 1 is a partial perspective view of the arrangement of the thermally conductive elements and thermoelectric devices for heating and cooling the container means of the present invention.
Figure 4:
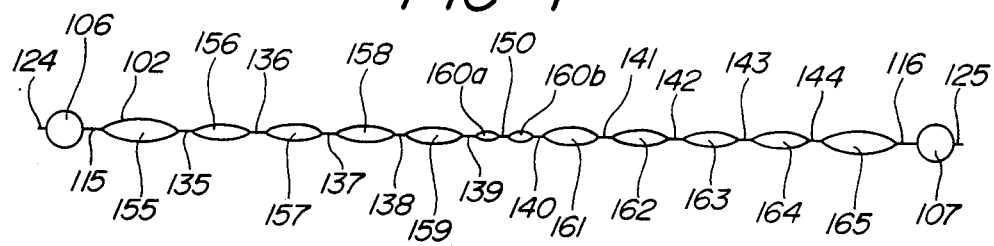
FIG. 4 is a cross-sectional view taken along line 4—4 of FIG. 2.
Figure 3:
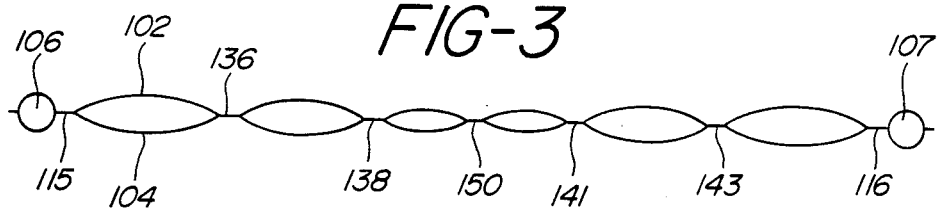
FIG. 3 is a cross-sectional view taken along line 3—3 of FIG. 2.
Figure 5:
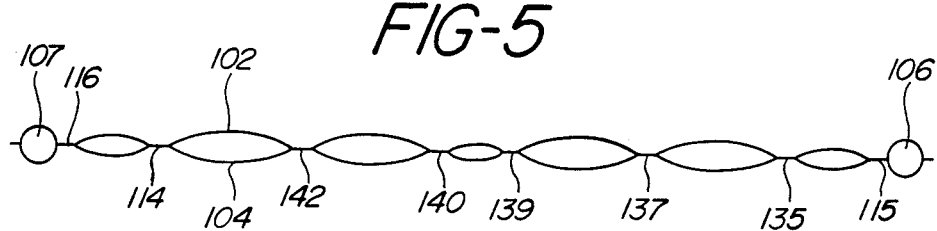
FIG. 5 is a cross-sectional view taken along line 5—5 of FIG. 2.

Referring now to FIGS. 1 and 6 of the drawings, there is shown an apparatus adapted to receive a container means in which or through which a liquid to be heated or cooled is contained or circulated. Apparatus 10 comprises a pair of substantially identical thermally conductive elements 14, 16. Thermally conductive element 14 has a first thermally conductive major surface 17 and a second thermally conductive major surface 18. Correspondingly, thermally conductive element 16 has a first thermally conductive major surface 19 and a second thermally conductive major surface 20. Thermally conductive elements 14, 16 have base portions 14a and 16a, respectively, as well as elevated portions 14b and 16b, respectively, the elevated portions having smaller areas than the base portions. Elements 14, 16 are conveniently machined from suitably sized pieces of aluminum, but it will be recognized that other conductive materials may be used for this purpose. In addition, it will be understood that the elevated portions and base portions may be made separately and subsequently fastened together, for example with screws. Thermally conductive elements 14, 16 are arranged in the apparatus in a spaced apart relationship such that their respective first thermally conductive major surfaces 17, 19 face each other so as to define therebetween a space 25 for receiving a container means in which heating or cooling may be effected. Elements 14, 16 are maintained in their desired spaced apart relationship by the use of spacer 26. A rabbet molding 28, preferably made of a nonheat-conductive material such as polyvinyl chloride, surrounds the periphery of base portions 14a and 16a so as to leave the first thermally conductive major surfaces completely free of any molding. Thus, referring to FIG. 1, first thermally conductive major surface 19 of thermally conductive element 16 and surface 28a of molding 28 are in the same plane.

Each of heating conducting elements 14, 16 has at least one thermoelectric device 30 for heating or cooling secured to its second major heat conducting surface. Such thermoelectric devices are commercially available from several companies in the U.S. and may be obtained in a range of wattage ratings for use with various direct current voltages. These devices have a pair of electrical lead wires for connection to the source of direct current. One electrical polarity allows the thermoelectric device to provide a cooling effect while the opposite electrical polarity allows the device to provide a heating effect.

In one embodiment, four thermoelectric devices 30, rated at thirty watts, were secured to each heat conducting element 14, 16 so that space 25, and the container means and fluid contained or flowing therein, could be heated to a temperature of about 38° C. or cooled to a temperature of about 2° C. The specific number of thermoelectric devices to be employed with any given apparatus depends on a variety of factors, among them the size and capacity of the device itself, the size of the thermally conductive elements, the volume of space 25, and the temperature range intended for that space. In one embodiment of the apparatus, the thermally conductive elements 14, 16 were machined from pieces of aluminum plate. Base portions 14a and 16a were 10 inches (25.4 cm.) long, 5 inches (12.7 cm.) wide, and ¼ inch (0.635 cm.) thick. Elevated portions 14b and 16b were about 8 inches (20.3 cm.) long, 2 inches (5.1 cm.) wide and ½ inch (1.27 cm.) thick. Thermoelectric devices 30 measured about 1½ inches (3.81 cm.) square by ⅛ inch (0.318 cm.) thick. As illustrated in FIG. 1, four of the thermoelectric devices 30 were secured to the remote surface of elevated portion 14b. Thus thermoelectric devices 30 were brought into heat-conducting contact with the second thermally conductive major surface 18 of thermally conductive element 16. Four thermoelectric devices 30 were secured to the remote surface of elevated portion 16b thus bringing those devices into heat-conducting contact with the second thermally conductive major surface 20 of thermally conductive element 16.

Apparatus 10 further comprises a pair of heat sinks 34 and 36. In the embodiment under discussion, the heat sinks have the same length and width as base portions 14a and 16a, and are about 2 inches (5.1 cm.) thick. The heat sinks, whose function is to remove heat in the cooling mode and cold in the heating mode, can be made of extruded aluminum. Preferably, the heat sinks comprise fins 40 to increase their efficiency.

Apparatus 10 also may advantageously include insulation material 45 which may, for example, be a closed cell polyurethane or polyester form. Other insulative materials may be used. The insulation has about the same thickness as that of elevated portions 14b and 16b and covers those regions of the second thermally conductive major surfaces of base portions 14a and 16a which are not contacted by either their respective elevated portions 14b, 16b, or molding 28 which extends inwardly about ¼ inch (0.635 cm.) from the peripheral edges of elements 14 and 16. Thus the insulation used would be in the form of a rectangle measuring about 9½ inches (24.1 cm.) long, 4½ inches (11.43 cm.) wide, and ½ inch (1.27 cm.) thick and having an interiorly located opening of about 8 inches (20.3 cm.) long and 2 inches (5.1 cm.) wide. It will be noted that the thickness of the insulation is substantially the same as the thickness of elevated portions 14b and 16b while the dimensions of the interiorly located opening therein is substantially the same as the outer dimensions of those elevated portions.

As shown in FIG. 6, elements 14 and 16 preferably have arcuate cutout portions 27 located in their first thermally conductive major surface 17 and 19, respectively. These cutout portions are located near each end of the elements 14, 16. In addition, molding 28 has a pair of cutout portions 29. It will be recognized that certain portions of FIG. 6 have, for purposes of clarity, been illustrated in larger than actual size. For example, space 25 in an actual embodiment of apparatus 10 can conveniently be about 60 mils wide and arcuate portions 27 and 29 can conveniently have a diameter of about ⅜ inch (0.95 cm.). It will be understood that space 25, arcuate cutout portions 27 and arcuate cutout portions 29 are adapted to receive the frame and container means combination shown in FIG. 2. Arcuate cut-out portions 29 at either end of the apparatus, along with space 25 therebetween, define a pair of generally circular openings 35 which are adapted to receive the opposed arms of the frame element. Cut-out portions 29 extend for nearly the entire length of the side portions of molding 28. The two cutout portions 27, along with space 25 therebetween define another pair of circular openings 38 which, when the frame and container means combination is fully inserted into space 25, are adapted to receive the inlet and outlet of the container means. Since, as will be seen hereinafter, the inlet and outlet have a short length, arcuate cut-out portions 27 need be cut only a short distance into elements 14, 16.

Referring to FIG. 7, there is shown a perspective view of a cabinet 60 which comprises, in addition to other components, apparatus 10 for heating or cooling. In this view, the entrance to space 25 of apparatus 10 is located substantially flush with the front panel 61 of the cabinet. The frame and container combination is shown in the process of being inserted, from front to back of the cabinet, into space 25. A portion of container means 100 adjacent its bottom edge 112 (which is not visible in FIG. 7) has been tensioned between rigid arms 82a, 82b of frame 80. As a result, the leading edge of the container/frame combination has been straightened, thus facilitating insertion of the combination into space 25. Thus, apparatus 10 has been made a permanent component in cabinet 61. The container means, being relatively inexpensive to construct, is preferably disposed of after a single use. The frame member can be disposable, in which case the frame/container combination would be supplied as a unit from the manufacturer or it can be adapted for multiple use. In the former event, the frame could be constructed of a rigid plastic; in the latter case, the frame is conveniently made from 5/16" steel rod or equivalent material.

Apparatus 10 advantageously may include a fan means (not illustrated in the accompanying drawings) for blowing air across heat sinks 34 and 36.

The assembly of apparatus 10 can be understood with reference to FIG. 6. Elements 14 and 16, as indicated earlier, are machined to the desired dimensions from single pieces of aluminum plate. Arcuate surfaces 27 are provided in the first thermally conductive surface of each element. Thermoelectric devices are positioned on the elevated portions 14b and 16b. If desired, a commercially available, thermally conductive grease may be placed between the lower surfaces of the thermoelectric devices and the upper surfaces of the elevated portions. Molding 28, with arcuate cutout portions 29 in the side portions thereof, is placed around elements 14, 16 as illustrated in FIG. 1 and secured to their peripheries with screws 42. Insulation 45 is put into place and the heat sinks are fastened to the thermally conductive elements by a series of screws 44, three of these screws being placed adjacent thermoelectric devices 30. When screws 44 are tightened, the thermoelectric devices are "sandwiched" between the heat sinks and the thermally conductive elements, assuring the necessary thermally conductive contact. The first thermally conductive major surfaces of elements 14, 16 are separated by a spacer 26 which has a thickness corresponding to the width desired for space 25. The device is bolted together with a series of nuts and bolts 26 passing through molding 28.

The electrical leads from the thermoelectric devices are connected in the desired polarity to a source of D.C. voltage. If it is desired to heat or cool at one's option, appropriate switch means are used in the electrical connections so that when the switch is in one position the proper polarity for cooling is provided and when the switch is in the other position, the proper polarity for heating is provided.

Figure 11:
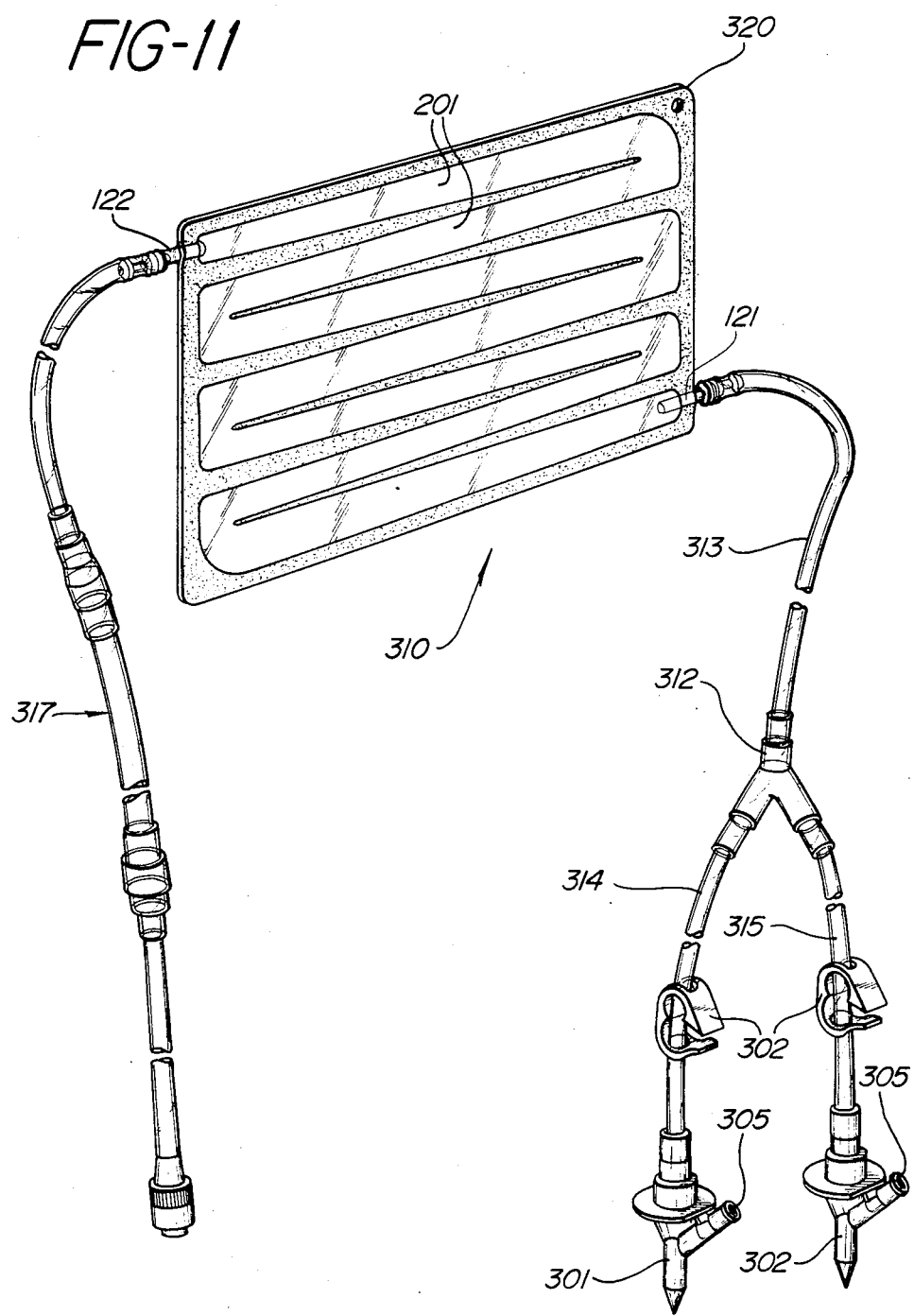
FIG. 11 is a perspective view of a preferred embodiment of the container means of the present invention.
Figure 12:
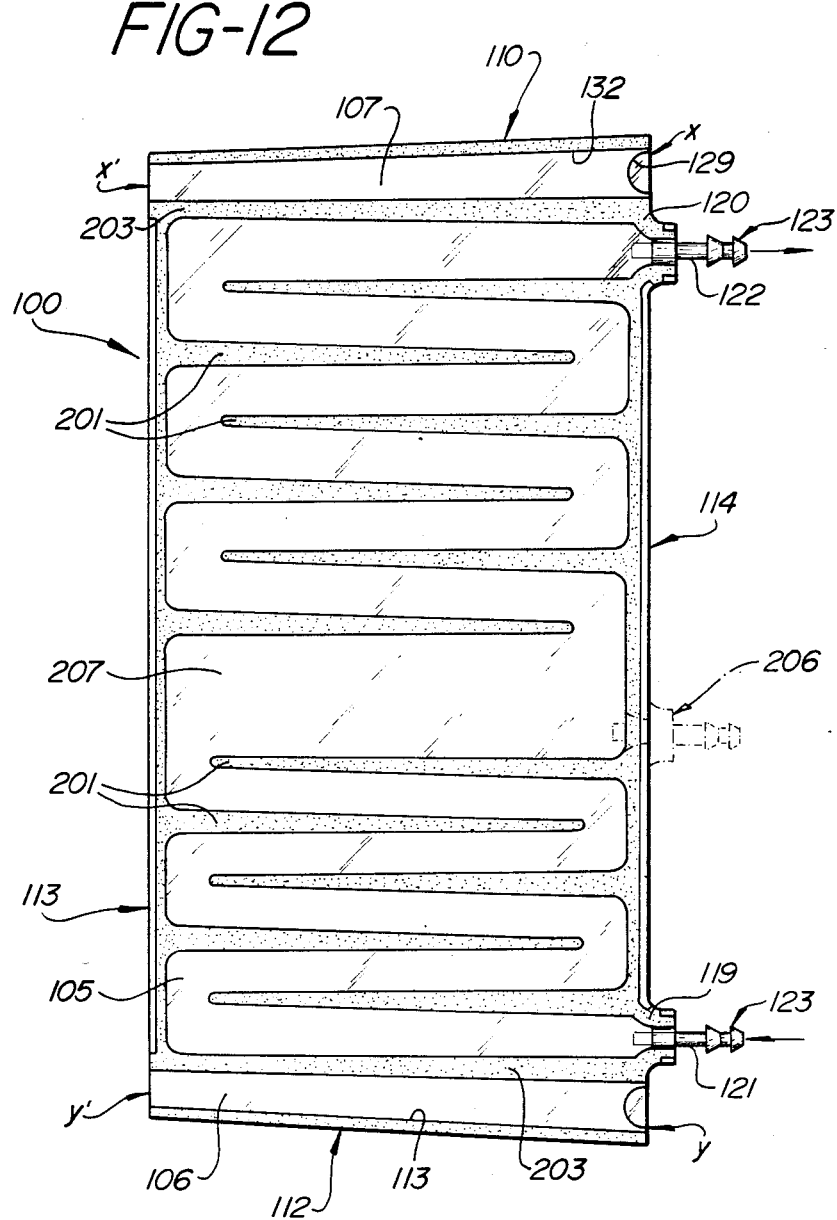
FIG. 12 is a cross-sectional view of the most preferred embodiment of the container means of the present invention.

With reference to FIGS. 2, 11 and 12 generally, the container means of the present invention is in the form of a generally flat bag whose two major walls comprising relatively thin, generally flexible sheets plastic material, such as polyethylene, polypropylene, polyvinyl chloride, poly(ethylene-vinyl acetate), nylon or the like, which are secured together in the manner explained hereinafter. The container means comprises a generally centrally located compartment for containing a liquid, and advantageously will include a pair of elongated tapered pockets 129 or sleeves, one said sleeve adjoining each side edge of that compartment, through which, as will be seen, the substantially parallel arms of a frame element may be inserted. The container comprises an inlet means 121 for introducing a liquid into the compartment and an outlet means 122 for withdrawing a liquid from the compartment.

The compartment for containing a liquid preferably includes means 201 for directing the flow of that liquid back and forth within the compartment. These flow directing means, which subdivide the compartment into a plurality of primary channels for the flow of liquid, preferably comprise a plurality of interiorly located attachment lines within the aforementioned compartment. As used herein, the term "attachment line" or "line of attachment" refers to a line along which the two sheets of plastic comprising the container means are secured together, for example, by heating sealing, gluing, or ultrasonic welding, heat sealing being preferred. Individual attachment lines of a first plurality are alternated with individual attachment lines of a second plurality so as to form a series of parallel channels through which a liquid can flow in a back-and-forth pattern.

The most preferred embodiments of the container means will, as shown in FIGS. 11 and 12, have attachment lines which are tapered in a continuous manner such that the width of the line of attachment decreases with increasing distance from the side wall of the container. These tapered walls are a particularly important feature of the present invention as they provide an air self-evacuating function. As fluid is introduced into the inlet 121, any trapped air previously existing in the container means will tend to form bubbles which will "roll along" the inclined plane due to buoyancy and continue thusly until their elimination through outlet means 122.

Each of the pockets 106, 107 or sleeves has an inner edge 203, which is adjacent the side edge of the compartment for containing a liquid, and an outer edge, which is near, or coincides with, the side edge of the container means. A preferred feature of the container means of the present invention is that its sleeves or pockets are tapered, that is, each pocket is wider at one end of the container means than it is at the other. The tapered pockets have two advantages. The first advantage is that the wider ends of the pockets make it easy to insert the opposed arms of a frame element. The second advantage is that, as the arms of the frame element are inserted further and further into the pockets, the portion of the container means between the narrower portions of the pockets becomes tensioned between the arms of the frame element. This tensioning provides a substantially straightened leading edge so that the bag and frame combination can be easily inserted into a narrow receiving slot such as space 25 of the earlier described apparatus for heating or cooling.

A preferred embodiment of the container means of the present invention is constructed from two substantially identical pieces or sheets 102, 104 of polyethylene plastic having a thickness of 5 mils. Each sheet 102, 104 of plastic has a top edge, an opposed bottom edge, a pair of opposed side edges connecting the ends of the top and bottom edges, and a pair of apron-like tabs projecting from the upper edge near each of the side edges. The two sheets of plastic are aligned and are then heat-sealed to each other along relatively narrow lines or bands of attachment to provide container means 100 comprising a compartment 105 for holding liquid and a pair of narrow sleeves or pockets 106, 107. For clarity, the lines or bands of attachment along which the two plastic sheets are attached to each other are shown in FIGS. 2, 11 and 12 as stippled lines. Heat sealing along lines of attachment 115, 116, 117, 118 provides liquid-tight edges for compartment 105, except for the presence of inlet 121 and outlet 122 (both discussed hereinafter).

As shown in FIG. 2, sheets 102 and 104 are additionally heat sealed along lines of attachment 124, 125 at side edges 113, 114 respectively of container means 100. Heat sealed regions 124 and 115 define the sides of one pocket or sleeve 106 at one side of the container and heat sealed regions 125 and 116 define the sides of a second pocket or sleeve 107 at the opposite side of the container. As shown in FIG. 2, pockets 106, 107 are open at both their ends and semicircular portions of plastic have been cut out of plastic sheet 102 to provide a notched portion 129 at the top of each sleeve or pocket in order to assist entry of the arms of frame element 80. It will be recognized that heat seal line 118 can be extended at its ends until it meets the lower ends of the heat seal lines 124, 125 if it is desired to provide closed ends for pockets 126, 127.

With further reference to FIGS. 2 and 12, upon completion of the heat sealing, there is provided container means 100 having an edge 110, an opposed edge 112, a pair of opposed edges 113, 114, and two apron-like tabs 119, 120. Tab 119 surrounds an inlet means 121 for introducing a liquid into compartment 105; similarly tab 120 surrounds an outlet means 122 for withdrawing a liquid from compartment 105. Inlet 121 and outlet 122 may be conveniently made of short lengths of polyethylene tubing having an inside diameter of about 0.12 inch (0.3 cm.) and an outside diameter of about 0.16 inch (0.4 cm.). The inlet and outlet preferably extend a short distance into compartment 105 and may have ridge portions 123 in order to provide a firmer grasp on tubing connected thereto. There must, of course, be a liquid tight seal at the inlet and outlet. This is accomplished in the preferred embodiment under discussion by heat sealing the apron-like tabs of sheets 102, 104 to each other and to the inlet and outlet tubes during the assembly operation. Alternatively, or as an adjunct to heat sealing, any suitable adhesive may be applied to the outer surfaces of the inlet and outlet in order to insure the necessary liquid tight seal. Thus, the heat sealing steps described above provide and define compartment 105 for holding liquid, the periphery of said compartment being designated by the letters a, b, c, d, e, f, g, and h in FIG. 2.

Figure 10:
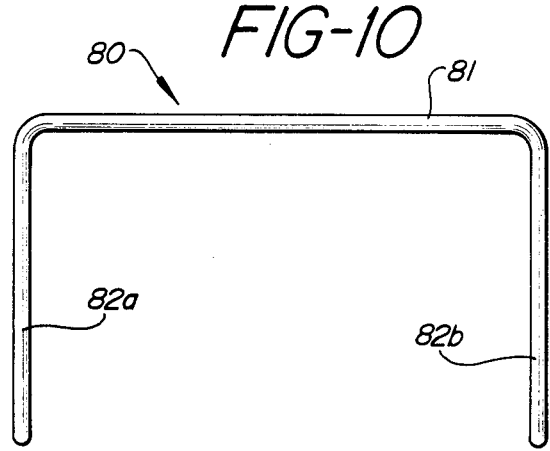
FIG. 10 is a plan view of a U-shaped frame member for the container means of the present invention.

As indicated earlier herein, pockets 106, 107 are provided at the sides of container means 100 in order to receive the arms of a frame element 80, illustrated in FIG. 10. This frame element, which in its simplest form is U-shaped and may be made of any suitable material, e.g., 5/16 inch steel rod bent into the required shape, comprises a cross member 81 and a pair of opposed, substantially parallel arms 82a, 82b. Pockets 106, 107 are tapered, that is, their width is greater at the top of the container means than their width at the bottom. Referring to FIG. 2, it will be seen that the outer edge 131 of pocket 106 coincides with and is defined by the inner edge of heat seal line 124; in the same way, the outer edge 132 of pocket 107 coincides with and is defined by the inner edge of heat seal line 125. In order to achieve the advantages of the present invention, pockets 106 and 107 will preferably have inwardly tapered outside edges 131 and 132 respectively. Stated differently, the desired tapered pockets are characterized by the fact that the straight-line distance, measured along top edge 110 from point x to point y, between outer edge 131 of pocket 106 and outer edge 132 of pocket 107 is greater than the straight-line distance, measured along lower edge 112 from point x' to point y', between outer edge 131 of pocket 106 and outer edge 132 of pocket 107.

Where container means 100 is to have a liquid flowing through it, for example, when the liquid is to be heated or cooled on a continuous basis, it is preferred in order to increase efficiency and minimize shunting to provide means for directing the liquid to flow back and forth in compartment 105. These flow directing means preferably comprise a plurality of lines or bands of attachment 135-144 in FIG. 2 and 201 in FIGS. 11 and 12 located interiorly of sides 115, 116 or 203 of compartment 105 and which define a plurality of primary channels 155-164 through which the liquid can flow. The lines of attachment can be formed by any of the aforementioned methods of gluing, ultrasonic welding or heat sealing, the latter method being preferred. Lines of attachment 135-144, 201 must be wide enough to retain their integrity when the container has a liquid in it. Making the lines of attachment wider than needed for the purposes of strength and integrity merely results in an undesirable and unnecessary reduction in the liquid holding capacity of compartment 105. It has been found that a width of ⅛ inch (0.32 cm.) is suitable for lines of attachment 135-144 in the embodiment in FIG. 2.

In the most preferred embodiments shown in FIGS. 11 and 12, the lines of attachment will be tapered from approximately ¼ inch to ⅛ inch. In the embodiment of FIG. 2, lines of attachment 135-144 all have a width of ⅛ inch (0.32 cm.) and are evenly spaced on a center-to-center basis within compartment 105 to provide a plurality of primary channels 156-164 for the flow of liquid. Each of channels 156-164 has a substantially similar width of about ¾ inch (1.9 cm.). Channel 155 (defined by lines of attachment 115 and 135) and channel 165 (defined by lines of attachment 116 and 144) are somewhat wider than channels 156-164; being about one inch (2.54 cm.) wide. It will be recognized that channels 155 and 156 need not be wider than channels 156–164; they could also have the same width as shown in the preferred embodiments of FIGS. 11 and 12, or be narrower.

The lines of attachment 135–144, 201 have a length which is greater than 50% and preferably more than 80% of the distance between the edges of the container.

In the most preferred embodiment shown in FIG. 12, the container 100 may be fitted with an additional inlet 206, shown in partial relief, for the addition of other fluids to be mixed with those fluids entering via inlet 121. For instance, as is typically the case in a heating mode where a patient's plasma has been treated through cryogellation, the very cold plasma is added to container 105 through inlet 121. It then undergoes partial heating prior to its arrival at inlet 206. The previously removed whole blood cell fraction is added through inlet 206 to be mixed with the partially warmed plasma in section 207 which may be enlarged to facilitate the mixing process. The plasma is preferably warmed in order to facilitate its mixing with the whole blood but may instead be mixed prior to addition to the container means as shown in FIG. 11. The substantially whole blood then continues to be warmed prior to its exit through outlet 122. The width of the channels are preferably adjusted in order to accommodate the respective volumes of the fluids and to obtain the desired flow patterns and heating (or cooling) of the fluids.

With reference to FIG. 2, it will be noted that lines of attachment 136, 138, 141, and 143 are placed somewhat closer to bottom heat seal line 118 than to top heat seal line 117, whereas lines of attachment 137, 139, 140, and 142 are placed somewhat closer to top heat seal line 117 than to bottom heat seal line 118. Although not illustrated in FIG. 2, the ends of lines 136, 138, 141, and 143 can be extended so they form a liquid tight junction with heat seal line 118, and the ends of lines 137, 139, 140, and 142 can be extended so they form a liquid tight junction with heat seal line 117. When the lines are so extended, liquid must flow to the end of one liquid flow channel before entering the next adjacent liquid flow channel. With the arrangement shown in FIG. 2, where lines 136, 138, 141, and 143 are spaced about 3/32" (0.24 cm.) from the edge of heat seal line 118 and lines 137, 139, 140, and 142 are spaced the same distance from heat seal region 117, the liquid flows primarily downwardly in one channel and upwardly in the next adjacent channel. In addition, there are secondary flow paths available where the lower ends of lines of attachment 136, 138, 141, and 143 are spaced from heat seal line 118 and where the upper ends of lines of attachment 137, 139, 140 and 142 are spaced from heat seal line 117. In FIG. 2, the wider arrows indicate primary liquid flow paths, and narrower arrows indicate secondary flow paths. This arrangement of the lines of attachment to provide for primary and secondary flow paths is particularly advantageous, e.g. when blood is flowing through the bag, because it minimizes regions in which the blood may stagnate.

In accordance with another feature of the embodiment shown in FIG. 2, one of the primary flow channels defined by a selected pair of interiorly located lines of attachment is reduced in width by interposing therebetween an additional line of attachment. This additional line of attachment 150 must be joined to either the top or bottom edge of the container means to form a liquid tight junction and is placed between lines of attachment 139 and 140. Line 150 is extended into heat seal line 118 at the bottom of the bag to form a liquid tight junction at that point. It will be appreciated that liquid flow channel 160 defined by lines of attachment 139, 140 is, by the interposition of the additional line of attachment 150, divided for nearly its entire length into two secondary liquid flow channels, 160a, 160b of reduced width. Container means 100 then has eight primary flow channels (156, 157, 158, 159, 161, 162, 163 and 164) of substantially equal width, two flow channels (155 and 165) of slightly larger width, and two secondary flow channels (160a, 160b) of reduced width. With this arrangement, the rate of flow of liquid through the narrower, secondary channels 160a, 160b is substantially greater than the rate of flow through the wider, primary channels. This increase in the rate of flow in the narrower channels is advantageous because it provides better liquid mixing and tends to increase the efficiency of the heating or cooling operation. As shown in FIG. 2, the two narrower channels formed by the interposition of line of attachment 150 are preferably located centrally of compartment 105.

Where only one pair of narrower, secondary flow channels is to be provided in the container means, it is preferred, as shown in FIG. 2, that the line of attachment (i.e., line 150) which subdivides the primary channel (i.e., channel 160) be located generally centrally of compartment 105. It is also possible to provide additional secondary flow channels where for example there are to be two pairs of narrower, secondary flow channels, it is preferred that the two subdividing lines and its nearer side edge of compartment 105 is equal to the distance between the other of the subdividing lines and its nearer side edge of compartment 105. For example, one of the subdividing lines of attachment can be located between lines of attachment 137 and 138 so as to subdivide primary channel 158 into a first pair of secondary channels and the other of the subdividing lines of attachment can be located between lines of attachment 141 and 142 so as to subdivide primary channel 162 into a second pair of secondary channels. When thus constructed, container means 100 has seven primary flow channels (156, 157, 159, 160, 161, 163 and 164) of substantially equal width, two flow channels (155 and 165) of somewhat larger width, and two separated pairs of secondary flow channels which, although not specifically labelled as such in the drawings, would be designated 158a, 158b and 162a, 162b.

The most preferred embodiments of the present invention, as shown in FIGS. 11 and 12, provide for fluid flow from substantially through inlet 121 at the bottom of container 105 to the top where the fluid exits through outlet 122. The physical arrangement of flow in this manner assists in the self-evacuating properties which form an important part of the present invention. The self-evacuating properties are particularly enhanced by the tapering walls 201 thereby assisting any entrapped air, likely to form bubbles, to "roll along" the walls whereby they may be flushed out of the container via the outlet.

With reference now to FIG. 11, an alternate embodiment of the most preferred form shown in FIG. 12 is depicted showing the connections likely with one form of use. Specifically, inlet 121 communicates via tubing 313 with a y branch connector 312 and from there through tubings 314 to connectors 301 and 302. These connectors are typical of those well-known in the art and are advantageously used to connect with standard replacement plasma bags also well-known. The connectors may be ideally outfitted with ports 305 for the hypodermic injection of drugs, medicines or other types of fluids. Clamps 302 provide flow rate control. The replacement plasma or other fluids flow through container 310, having tapered walls 201 to assist the self-evacuation of air, and may be suitably warmed by contact or juxtaposition with heating elements. The fluids exit container 310 through outlet port 122 and communicate via tubing 317 to a connector 303 which may be any type of connector suitable for returning the fluids to the patient. In the embodiment depicted, the connector is a standard Luer lock type connector which will communicate with other tubing and hypodermic arrangements (not shown) for return of the fluids to the patient. FIG. 11 further depicts an alternative arrangement for holding the container such as by means of hanging via a pin 320 and clamping arrangements (not shown) around inlet 121 and outlet 122. Such an arrangement may be preferable inasmuch as it eliminates the need for pockets for receiving the arms of an otherwise required frame element. Still other similar alternatives may be readily conceived by those skilled in the art without significantly affecting the operation or scope of the present invention.

Figure 8:
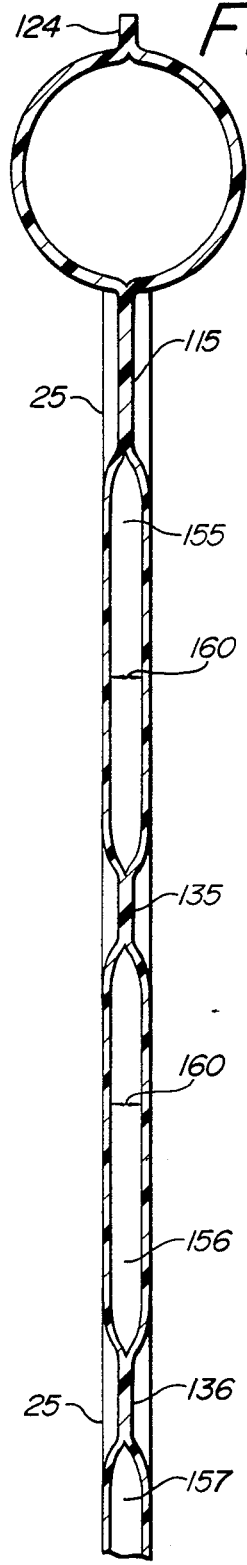
FIG. 8 is a partial view, greatly enlarged and partially in cross-section, of a container means positioned in the apparatus of FIG. 6.

FIG. 8 is a partial cross-sectional view, greatly enlarged, showing container means 100 in its position in space 25 of apparatus 10. The container is illustrated in the configuration which it assumes when placed in space 25 and with a liquid in it. The degree to which compartment 105 of the container expands due to the force of the liquid therein is restricted and effectively controlled by the width of space 25, which in a preferred embodiment described earlier herein is 60 mils. Thus it will be seen that the flow channels, typified in FIG. 8 by channels 155 and 156, have assumed a rectangular shape with more or less rounded end portions.

If, as described earlier herein, container means 100 is constructed of 5 mil thick sheets of plastic and space 25 measures 60 mils, then the maximum thickness 160 of the liquid flow channels is about 50 mils. The foregoing dimensions allow for acceptable priming volumes and for efficient heat transfer to or from the liquid in the container at liquid flow rates of up to 200 cc. per minute. Those skilled in the art will recognize that if the liquid flow rate is kept constant and the effective thickness 160 is reduced, the priming volume will be reduced, heat transfer efficiency will increase, and the turbulence of the flow will increase. While reduced priming volume and increased heat transfer efficiency may be advantageous, increased turbulence might not be desirable or acceptable as, for example, where blood is being heated or cooled since foaming is to be preferably avoided. On the other hand, if the system must handle higher flow rates, it will probably be necessary, if it is desired to avoid turbulence, to increase thickness 160 and accept whatever increase in priming volume and reduction in heat transfer efficiency accompanies that increase.

Figure 9:
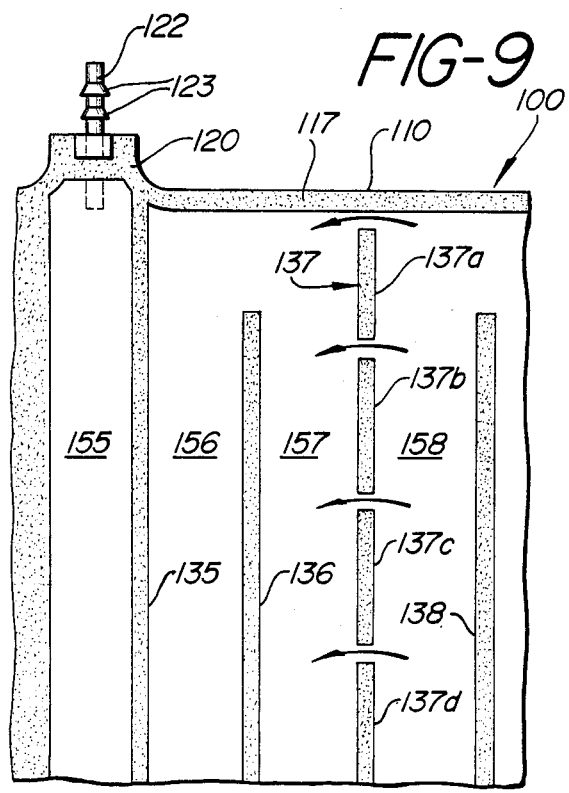
FIG. 9 is a partial view of an alternate embodiment of a container means of the present invention.

Referring now to FIG. 9, there is shown an alternative construction wherein line of attachment 136 comprises a plurality of smaller lines of attachment 137*a*, 137*b*, 137*c*, and 137*d* having small gaps therebetween. Such a construction can be used where it is desired to provide secondary flow paths between adjoining channels.

The container means of the present invention can, if desired, be provided with two lengths of tubing, 66*a*, 66*b* one being connected to inlet 121 and the other to outlet 122 (see FIG. 7). The unconnected ends of these lengths of tubing may carry tubing connectors for connecting inlet 121 to a source of liquid and for connecting outlet 122 so that the liquid may be sent to additional pieces of equipment for further processing or, if appropriate, returned to the patient.

If container means 100 is intended for use with body fluids, such as blood or plasma, which must not be contaminated, than those portions of the container means (and tubing, connectors, etc. which may be associated therewith) must be made from non-contaminating, body fluid compatible raw materials.

What is claimed is:

1. A flexible container means adapted to be received by a frame means, having a cross member from which extends a pair of substantially parallel arm elements, and in which a liquid may be stored or through which a liquid may be circulated, said container means comprising a pair of walls including two relatively thin, generally flexible sheets of a polymeric material, a top edge, a bottom edge, a centrally located compartment for containing said liquid, an elongated sleeve adjoining each top and bottom edge of said compartment for receiving said arm elements, inlet means for introducing said liquid into said compartment and outlet means for withdrawing said liquid from said compartment, each of said sleeves having an inner edge and an outer edge, the straight-line distance between the outer edges of said sleeves on one side of the container means being greater than the straight-line distance between the outer edges of said sleeves along the opposing side of said container means, said container means further including means for dividing said compartment into a plurality of channels of substantially constant width for the flow of liquid therethrough, said means for dividing being tapered whereby any air bubbles entrapped within said compartment will flow with said liquid and be evacuated from said compartment upon withdrawal of said liquid through said outlet means.

2. Container means according to claim 1 in which the inlet means and the outlet means are located along a side edge of side container means.

3. Container means according to claim 2 in which said elongated sleeves are coextensive with the side edges of said compartment.

4. Container means according to claim 1 in which said two sheets of polymeric material comprising the walls of said container are joined to each other along relatively narrow, tapered lines of attachment located interiorly of said compartment whereby a plurality of channels for the flow of liquid is provided in said compartment.

* * * * *